United States Patent
Frenkel et al.

(10) Patent No.: US 6,168,699 B1
(45) Date of Patent: Jan. 2, 2001

(54) EASY TO HANDLE ELECTROCHEMICAL SENSOR IN THE SHAPE OF A STRIP

(75) Inventors: Erik Jan Frenkel, Neuchâtel; Gérard Jaeger, Blonay, both of (CH)

(73) Assignee: Asulab S.A., Bienne (CH)

( * ) Notice: Under 35 U.S.C. 154(b), the term of this patent shall be extended for 0 days.

(21) Appl. No.: 09/414,422

(22) Filed: Oct. 7, 1999

(30) Foreign Application Priority Data

Oct. 9, 1998 (EP) .................................... 98119146

(51) Int. Cl.$^7$ .................................... G01N 27/26
(52) U.S. Cl. .................. 204/400; 504/416; 504/403; 422/82.01
(58) Field of Search .................. 204/403, 416, 204/431, 433, 400; 422/82.01, 82.02, 82.03, 56

(56) References Cited

FOREIGN PATENT DOCUMENTS

| | | |
|---|---|---|
| 645627 | 3/1995 | (EP) . |
| 787984 | 8/1997 | (EP) . |
| 87 00286 | 1/1987 | (WO) . |

*Primary Examiner*—T. Tung
*Assistant Examiner*—Alex Noguerola
(74) *Attorney, Agent, or Firm*—Sughrue, Mion, Zinn, Macpeak & Seas, PLLC

(57) ABSTRACT

Electrochemical sensor, in the shape of a strip of small dimensions including a thin plastic substrate (1) carrying, over all or part of its length, at least two current collectors (4, 5) separated by an electrically insulating space (3), said substrate (1) and said collectors (4, 5) being covered with a plastic coating (2), in which two windows (8, 9) are cut allowing collector portions (4, 5) to appear to form a connection window (8) at one end and a measuring window (9) close to the other end, leaving a distal portion (10) of the strip free beyond the measuring window, wherein said distal portion (10) includes, on the side of the strip where the windows (8, 9) are arranged, at least one button (12) obtained by hot or cold deformation (11) of the external face of the substrate (1), said button allowing said sensor to be slid to the edge of a flat surface to be grasped.

7 Claims, 1 Drawing Sheet

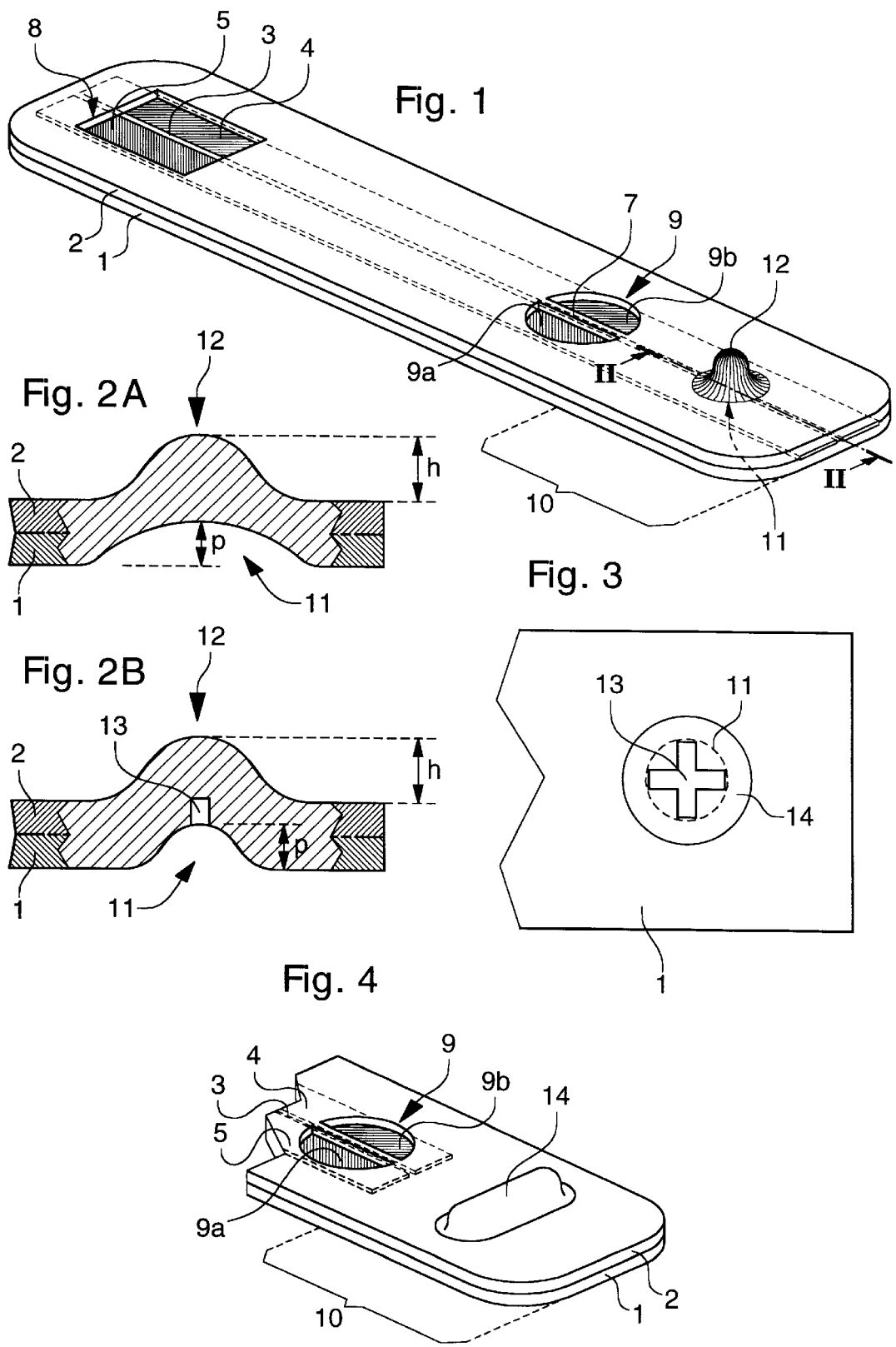

ically allowing biological parameters to be determined or the concentration of a constituent in solution to be measured. -->

EASY TO HANDLE ELECTROCHEMICAL SENSOR IN THE SHAPE OF A STRIP

BACKGROUND OF THE INVENTION

The present invention concerns an electrochemical sensor in the shape of a strip which is easy to handle, for example to grasp from a flat surface and insert into an electronic apparatus allowing biological parameters to be determined or the concentration of a constituent in solution to be measured.

Reagent strips relying on a chemical reaction modifying a colour, designated by the general term <<chemical sensors>> or <<colorimetric sensors >>, are commonly used for a large number of chemical or biological determinations or dosages and do not involve any particular handling difficulties when such sensors are in the form of a roll from which a portion is detached and one end thereof is dipped into the solution to be analysed. Such sensors are easy to handle since they are generally kept in the hand until the coloured reaction has developed, and they are then discarded. When these sensors are packaged in individual pouches, the user can have difficulty in opening the pouch. When they are not individually packaged, and they are either stacked in a box or placed loose in a tube, it is often difficult to remove a single sensor from the packaging because of the possibility of them sticking to each other.

However, in order to make handling easier in the event that the sensor is nonetheless placed on a flat surface, U.S. Pat. No. 5,008,077 proposes a chemical sensor which is easier to grasp by tipping it. This sensor is formed of an elongated plastic support, one end of which carries the reagent material and the other end, by which it has to be grasped, is at a distance from the flat surface on which it rests, either by bending, for example bending, said end, or by deforming the plastic material between said end to be grasped and the reagent material to form over a large part of the width thereof a raised portion oriented towards the flat surface, i.e. a raised portion situated on the face of the sensor opposite that which carries the reagent material.

The above arrangement is not satisfactory for an electrochemical sensor in that it includes at least two current collectors connecting a contact zone arranged at one end and at least one measuring zone arranged at a certain distance on the sensor. These collectors occupy a very large part of the width of the plastic support and are formed by excessively thin conducive materials, deposited on said support by laminating a metallised plastic film or by screen printing a conductive paste. Such collectors, whose thickness of the order of several tens of microns would be damaged by any bending or stamping of the surface of the plastic support over too large a part of its width.

SUMMARY OF THE INVENTION

An object of the invention is to overcome the drawbacks of the aforementioned prior art by providing an electrochemical sensor which is easy to grasp from a flat surface with the possibility of sliding it to the edge of said surface. The invention also concerns a sensor of this type which can only be inserted into an electronic apparatus in one direction, and which allows a poor sighted person to discern which side of the sensor carries the measuring zone and the contact zone and to identify easily the location thereof without touching them. According to another aspect, the electrochemical sensors according to the invention can be packaged by stacking them in a box without any risk of two sensor sticking to each other.

The invention thus concerns an electrochemical sensor for determining biological parameters, or measuring the concentration of a constituent in solution, in the shape of a strip of small dimensions including a thin plastic substrate carrying, over all or part of its length, at least two current collectors separated by an electrically insulating space. The substrate and the collectors are covered with a plastic coating, in which two windows are cut allowing collector portions to appear to form a connection window at one end and a measuring window close to the other end, leaving a distal portion of the strip free beyond the measuring window. This sensor is characterised in that said distal portion includes, on the side of the strip where the windows are arranged, at least one button obtained by hot or cold deformation of the external face of the substrate.

For an electrochemical sensor and in particular a sensor intended for measuring a biological parameter, such as the blood glucose level, it is necessary, after having removed it from its packaging onto a flat surface, to be able to grasp it delicately in order to insert it into a measuring apparatus, and then deposit a drop of the test solution, such as a drop of blood.

The sensor according to the invention allows this object to be achieved by being able, thanks to a button in relief on the surface of the sensor including the contact zone and the measuring zone, to slide it to the edge of the flat surface, for example to the edge of a table. According to a preferred embodiment, this deformation is performed in such a way that the height of the button with respect to the external surface of the coating is greater than the depth of the envelope of the deformation effected in the substrate with a punch allowing a small quantity of plastic material to be pushed back to form the button. In the detailed examples hereinafter several embodiments of the invention will be given by way of example. As is clear, if one wishes to manufacture such sensors in batches in the most economical way, they will all have the button and corresponding deformation at the same location. If they were packaged in stacks, there would be a risk of them being assembled like snap fasteners if the shape of the deformation were exactly the same as that of the button. This preferred embodiment allows this drawback to be avoided by always arranging, over at least a portion of their length, a space between two stacked sensors which would have buttons and deformations at exactly the same place.

When the sensors are manufactured with collectors extending from one end of the support to the other, the grasping button is preferably arranged in the region of the insulating space. Further, it is possible to position the button randomly anywhere on the length of the insulating space situated in the distal portion.

It is also possible to manufacture sensors in batches, with the collectors not in the distal portion or omitted completely. It is then possible to arrange the grasping button randomly anywhere on the surface of the distal portion. It is even possible to arrange several buttons able to form together a grasping bar over all or part of the width of the sensor.

BRIEF DESCRIPTION OF THE DRAWINGS

Other features and advantages of the invention will appear more clearly upon reading the following detailed description, with reference to the annexed drawings in which:

FIG. 1 is a perspective diagram of an electrochemical sensor according to the invention;

FIG. 2A is an enlarged cross-section along the line II—II of FIG. 1 of a first embodiment of the grasping button;

FIG. 2B is an enlarged cross-section along line II—II of FIG. 1 of a second embodiment of the grasping button;

FIG. 3 is a bottom view of the deformation forming the button shown in FIG. 2B;

FIG. 4 is a perspective diagram of another embodiment of a sensor according to the invention.

DETAILED DESCRIPTION OF THE INVENTION

FIG. 1 shows by way of example an electrochemical sensor allowing the blood glucose level to be determined by amperometry, i.e. measuring techniques. The sensor includes a thin plastic substrate 1, made for example of PET, carrying over its entire length two current collectors 4, 5 separated by a small space 3 which electrically insulates the two collectors 4, 5. The nature of these collectors 4, 5 and the way that they are applied onto the substrate are well known to those skilled in the art, the method consisting for example in laminating two metallised insulating films, using different metals for collector 5 which will form working electrode 9a and collector 4 which will form reference electrode 9b. The well known combination Pt—Ag/AgCI will for example be used. Substrate 1 and collector/electrodes 4, 5/9a, 9b are coated with a insulating coating 2 in which two windows 8, 9 are cut, for example by stamping, allowing collector portions 4, 5 to appear. A first window 8 is situated at one end of the sensor and allows it to be electrically connected to a measuring apparatus by being inserted in an opening provided for this purpose. A second window 9 arranged close to the other end delimits a measuring window allowing electrodes 9a, 9b to appear. In the example chosen, a reagent composition including for example a glucose oxidase (GOD) will be applied to measuring electrode 9a and a mediator allowing the electrons to be transferred, for example in accordance with the teaching of U.S. Pat. No. 5,378,628. The sensor, or more precisely substrate 1 and coating 2, is extended beyond measuring window 9 by a distal portion 10 which allows the sensor to be grasped, without connection window 8, nor measuring window 9 being touched, so as to insert it in the measuring apparatus. In order to allow or facilitate the grasping of the sensor this distal portion 10 is provided with a button 12, obtained by a deformation 11 of substrate 1 and coating 2, which, by the application of a finger, allows it to be easily slid to the edge of a flat surface.

This button 12 can be obtained in different ways, but according to another aspect of the invention with reference to FIGS. 2A and 2B, it is made by a hot or cold deformation 11 of the external face of the substrate, so that the height h of said button 12 is greater than the depth P of deformation 11. As shown in FIG. 2A, in which substrate 1 and coating 2 are shown fused by the assembly of the sensor, this result is obtained by effecting the deformation by means of a punch whose rounded end has a greater radius of curvature than that of a die placed on the side of the coating and corresponding in recess to the desired shape of the button. According to another embodiment shown in FIG. 2B, the punch used can have substantially the same radius of curvature as that desired for button 12, but have at its end an axial extension with a support crown 14 arranged at its periphery. This axial extension is for example in the shape of a cross, as shown in FIG. 3. It can also be given any other shape, such as an alphanumerical sign which can be read under the sensor, and for example representing a feature of said sensor. This axial extension of the punch generates an indentation 13 in the bottom of the envelope of deformation 11, by moving additional plastic material to give button 12 a height h greater than depth p of deformation 11. The envelope of deformation 11 will thus be smaller than that of button 12.

The cross-sections in FIGS. 2A, 2B concern a sensor wherein current collectors 4, 5 are arranged over the entire length of substrate 1, essentially because of batch manufacturing economic imperatives. The collector portions situated in distal portion 10 have no technical function, but are liable to short-circuit the sensor if the deformation causes movement of said collectors. For this reason, button 12 is preferably positioned in the region of insulating space 3, and can according to the manufacturer's choice occupy a random place along this line, including for sensors from a same manufacturing batch.

With reference now to FIG. 4, distal portion 10 is shown of a sensor wherein current collectors 4, 5 have been interrupted, for example by abrasion of said collectors 4, 5 in this portion. The short-circuiting risk mentioned previously no longer exist, and one or more buttons can occupy a random place on said distal portion 10. As shown, it is even possible for several buttons 12 together form a bar 14, said bar 14 then being obtained with a punch having the appropriate shape.

The preceding examples, given by way of non limiting illustration, show that it is possible, without thereby substantially increasing the manufacturing cost, to manufacture electrochemical sensors which are easier to handle, easier to package and whose button also has a <<polarising>>function, given that the slot of the measuring apparatus into which it has to be inserted always corresponds exactly to the cross-section of the sensor.

The preceding description was essentially made with reference to an electrochemical sensor for glucose level measurements, but those skilled in the art can, without departing from the scope of the invention, make the necessary adjustments for any other type of electrochemical sensor relying on conductimetric, voltametric, coulometric or polarographic measurements, to determine or measure other chemical or biological parameters.

What is claimed is:

1. An electrochemical sensor for determining biological parameters, or measuring the concentration of a constituent in solution, in the shape of a strip of small dimensions including a thin plastic substrate carrying, over all or part of its length, at least two current collectors separated by an electrically insulating space, said substrate and said collectors being covered with a plastic coating, in which two windows are cut allowing collector portions to appear to form a connection window at one end and a measuring window close to the other end, leaving a distal portion of the strip free beyond the measuring window, wherein said distal portion includes, on the side of the strip where the windows are arranged, at least one button obtained by hot or cold deformation of the external face of the substrate, which allows said sensor to be handled more easily.

2. An electrochemical sensor according to claim 1, wherein the height h of said at least one button above the coating is greater than the depth p of the envelope of the deformation of the substrate.

3. An electrochemical sensor according to claim 2, wherein the difference between the values h and p is obtained by an indentation of the bottom of the envelope of the deformation, the button and the deformation being then able to have substantially the same radius of curvature.

4. An electrochemical sensor according to claim 2, wherein the difference between the values h and p is obtained by having a greater radius of curvature for the deformation than that of a button.

5. An electrochemical sensor according to claim 1, wherein the collectors are arranged over the entire length of the sensor and in that a button is arranged in the region of the insulating space.

6. An electrochemical sensor according to claim 1, wherein the collectors are interrupted in the distal portion and in that at least one button is formed at a random location in said distal portion.

7. An electrochemical sensor according to claim 1, wherein several buttons together form a bar.

* * * * *